United States Patent [19]

Russin

[11] Patent Number: 5,795,308
[45] Date of Patent: Aug. 18, 1998

[54] APPARATUS FOR COAXIAL BREAST BIOPSY

[76] Inventor: Lincoln D. Russin, 440 Westhampton Rd., Northampton, Mass. 01060

[21] Appl. No.: 690,185

[22] Filed: Jul. 26, 1996

Related U.S. Application Data

[63] Continuation-in-part of Ser. No. 386,111, Mar. 9, 1995, abandoned.

[51] Int. Cl.$^6$ .................................................. A61B 5/00
[52] U.S. Cl. ............................................... 600/567
[58] Field of Search ........................... 128/749, 751–754; 606/167, 170

[56] References Cited

U.S. PATENT DOCUMENTS

| | | |
|---|---|---|
| 4,007,732 | 2/1977 | Kuaule et al. . |
| 4,461,305 | 7/1984 | Cibley . |
| 4,651,752 | 3/1987 | Fuerst . |
| 4,682,606 | 7/1987 | De Caprio ............... 128/754 |
| 4,691,333 | 9/1987 | Gabriele et al. . |
| 4,727,565 | 2/1988 | Ericson . |
| 4,821,727 | 4/1989 | Levene et al. . |
| 4,837,795 | 6/1989 | Garrigus . |
| 4,966,583 | 10/1990 | Debbos . |
| 5,074,311 | 12/1991 | Hasson . |
| 5,083,570 | 1/1992 | Masby . |
| 5,133,360 | 7/1992 | Spears ..................... 128/754 |
| 5,148,813 | 9/1992 | Bucale . |
| 5,172,702 | 12/1992 | Leigh et al. . |
| 5,183,463 | 2/1993 | Debbas . |
| 5,188,118 | 2/1993 | Terwilliger . |
| 5,267,572 | 12/1993 | Bucalo . |
| 5,316,014 | 5/1994 | Livingston . |
| 5,353,804 | 10/1994 | Kornberg et al. ........ 128/754 |
| 5,415,169 | 5/1995 | Siczek et al. . |
| 5,445,645 | 8/1995 | Debbas . |
| 5,452,367 | 9/1995 | Bick et al. . |
| 5,499,989 | 3/1996 | LaBash . |
| 5,507,298 | 4/1996 | Schramm et al. . |
| 5,526,822 | 6/1996 | Burbank et al. . |
| 5,570,699 | 11/1996 | Kass . |
| 5,573,008 | 11/1996 | Robinson et al. ......... 128/754 |

Primary Examiner—Max Hindenburg
Attorney, Agent, or Firm—Richard J. Birch

[57] ABSTRACT

A device and method for coaxial breast biopsy utilizing a rigid rod. The suspected cancer is pierced by a rigid rod which stabilizes the cancer in the path of a cutting cannula and provides mechanical guidance for the cannula as it incises a cylinder of tissue centered on the rod. The rigid rod has retractable anchor hooks and a spiked collar to slide over the rod. The cancer is bracketed by the anchor hooks distally and the spiked collar proximally to stabilize it on the rod and mark its position for excision by the cannula. Associated tools enable insertion and positioning of the rod with anchor hooks and the spiked collar while the cutting cannula employs an internally situated snare wire to sever the specimen from the breast once it has been incised by the cannula. A reel mechanism or hemostat is used to tighten the snare wire. The location of the biopsy within the breast is marked with a spring clip and clip injector in case further therapy is required. An incision from the skin down to the location of the spiked collar is made with a power scalpel with an oscillating circular blade. A stabilizing device is utilized to facilitate the initial incision in the breast and subsequent passage of the cutting cannula.

12 Claims, 22 Drawing Sheets

5,795,308

1

APPARATUS FOR COAXIAL BREAST BIOPSY

CROSS-REFERENCE TO RELATED APPLICATION

The present application is a Continuation-in-Part application of application Ser. No. 08/386,111, filed Mar. 9, 1995 for Biopsy Device and Method, now abandoned.

BACKGROUND OF THE INVENTION

As currently performed, open surgical biopsy of suspected breast cancer is guided by a flexible hook-wire which is embedded into the cancer by means of radiologic (mammographic or ultrasound) imaging. The surgeon makes an incision into the breast, finds the area of tissue where the hook-wire is embedded, and removes it as a biopsy specimen. Because the surgeon can not see the tip of the embedded hook-wire (it is considered undesirable to cut through the suspected cancer) and also because the hook-wire is a flimsy anchor which can be easily dislodged from its position within the breast, removal of the biopsy specimen involves some guess work which results in a degree of inaccuracy and imprecision. Suspected cancers are often incompletely excised, and occasionally are missed altogether.

With Coaxial Biopsy as described in patent application Ser. No. 08/386,111, a rigid rod is inserted through the suspected cancer with guidance provided by radiologic imaging. The rigid rod is a K-wire, a common surgical tool, which may have a diameter three to six times greater than the standard flexible hook-wire used for needle localization of non-palpable breast masses prior to open surgical excision. The rod establishes a mechanical guide over which the biopsy device is advanced, like a train rolling down a rail, and stabilizes the cancer in the path of the cutting instrument so that it will be removed by the biopsy process.

The concept of rigidity of the rod is central to Coaxial Biopsy as described in the parent application. While a flexible hook-wire may indicate the location of the suspected cancer, one skilled in the art would know that a hook-wire can not provide mechanical guidance for the cutting tool, nor can it stabilize the cancer in the path of the cutting device. The difference between hook-wire guided biopsy and Coaxial Biopsy is perhaps best understood by analogy: one can catch fish with a hook on the end of a flexible fishing line, or one can spear the fish with a barbed harpoon on a long handle. Both systems are superficially similar in that they hook into the fish at some point, but one is flexible and the other is rigid. The cutting device (the cannula) is concentrically positioned along the rod; the rod guides the cannula to the cancer.

What has been disclosed previously in the parent application is a method of marking the location of a suspected cancer so it can be identified with radiologic imaging (either by x-ray fluoroscopy or by ultrasound); normally the cancer is not clearly visible except by mammographic imaging. A metal target implanted into the immediate vicinity of the suspected cancer can be seen by fluoroscopy or ultrasound. The advance of a scalpel blade cutting a path down the rod to a point just proximal to the metal target and the progress of the cannula as it slides over the rod and incises the specimen containing the target are monitored radiologically, eliminating the guess work associated with standard hook-wire guided biopsy. This method is advantageous compared with stereotactically-guided biopsy because it can be performed without the need for a special stereotactic x-ray table. All that is required is a mammography machine for placement of the rod and the target, and an ultrasound or fluoroscopic machine for monitoring the biopsy in the operating room. While this is preferable to stereotactic biopsy and standard surgical biopsy with hook-wire guidance, the requirement for an operative ultrasound or fluoroscopic machine is a relative disadvantage, since not all surgeons are familiar with fluoroscopic or ultrasound imaging.

Also disclosed previously are cutting cannulae with internal snare mechanisms. However, these require at least two concentrically positioned cannulae to maintain the snare wire between them; the inner cannula in these prior patents is then withdrawn to reveal the snare wire, which is then tightened to amputate the specimen. These internal-snare devices require multiple moving parts, and share the disadvantage of complexity associated therewith.

The snare previously disclosed as part of the Coaxial Biopsy system is an external snare slipped over the outside of the cannula by a modification of an existing tonsil-snare device. While this works effectively, it requires an initial relaxing incision to be made along the cannula to pass the device through, and it is a separate tool. If a simpler internal snare mechanism could be devised, this would incorporate two tools into one by combining the cannula and the snare device.

Examples of prior art surgical apparati and procedures for performing biopsies can be found in U.S. Pat. No. 5,353,804 for Method and Device for Percutaneous Excisional Breast Biopsy issued Oct. 11, 1994 to Kornberg, et al and U.S. Pat. No. 5,133,360 for Spears Retriever issued Jul. 28, 1992 to Colin P. Spears and in the prior art cited these patents.

It will be appreciated that there exists a continuing need for improvement in breast biopsy which is partially satisfied by the Coaxial Biopsy system disclosed in the parent application. However, additional improvements of Coaxial Biopsy to enable intra-operative location of the suspected cancer without additional fluoroscopic or ultrasound imaging, and amputation of the specimen by an improved internal snare mechanism would be useful. Also, a method of injecting a metal clip into the breast to mark the location of the biopsy would be helpful in case further therapy such as wider surgical excision is needed. Finally, a stabilization device to position the breast most conveniently during Coaxial biopsy would be useful.

SUMMARY OF THE INVENTION

A Coaxial Biopsy system enables biopsy without need for intra-operative radiologic imaging. The system comprises:

(1) A stiff, sharpened rod with a conical point to penetrate and impale the suspected cancer;

(2) A tube with a bevelled edge at one end to slip over the sharpened rod, which establishes a portal into the breast after the rod is removed;

(3) An anchor-rod with flexible metal hook-wires welded to one end, which can be compressed and inserted into the proximal (external end) of the tube, and extruded through the other end of the tube to form an anchor in the breast just distal to the cancer which prevents forward or backward displacement of the rod;

(4) A microscalpel with a tube handle to slip over the rod with anchor hooks, to incise a short radial incision along the rod to a point just proximal to the location of the suspected cancer;

(5) A spiked metal collar with several short segments of flexible wire welded to it radially, to provide "spikes" which will embed into the breast tissue and stabilize the collar along the rod in the breast just proximal to the suspected cancer;

(6) An inserting tool for the spiked collar consisting of a tube with a collar welded near one end. The spiked collar slips over the end of the tube, but is stabilized by the welded collar so that when the spiked collar-inserting tool assembly is slid over the anchor-rod, the spiked collar can be advanced over the anchor-rod into the breast. When the inserting tool is withdrawn the spikes embed in the adjacent breast tissue and maintain the spiked collar in position on the rod just proximal to the cancer;

(7) A power scalpel with a circular blade attached to a handle and an arm attached to the blade by a pivot. A motor in the handle provides the arm with a reciprocating motion, which causes the blade to rotate in a short arc in a back and forth motion. The blade has a diameter of 1–3 cm and is useful for creating an incision centered on the rod from the skin down to the embedded collar with spikes;

(8) A cutting cannula sharpened at the distal end to form a circular knife with an internal circumferential groove near the cutting edge to accommodate a snare wire stabilized in place by the spring action of the wire or by an adhesive glue, with a hole for the snare wires to exit and be pulled when the snare is tightened to amputate the specimen within the cannula and with a longitudinal groove to lodge the wire strands in along the shaft of the cannula;

(9) An outer tube to slip over the shaft of the cannula to maintain the wire strands in the longitudinal groove prior to tightening the snare;

(10) A reel mechanism for drawing the ends of the snare sire tight to close the snare and amputate the tissue in the cannula;

(11) A self-attaching spring clip made of flexible steel wire for embedding into breast tissue to mark the site of a coaxial biopsy within the breast;

(12) A clip injector tool to position the self-attaching clip alongside the cannula at the site of the biopsy; and,

(13) A breast stabilizing device with a flat disc on one tong and two finger-like tines on the other, handles on the proximal ends, to form tongs joined by a central pivot and governed by a ratchet mechanism. The action of this hinged tong device compresses and stabilizes the breast to facilitate the incision along the rod for passage of the coaxial cannula.

DESCRIPTION OF THE PREFERRED EMBODIMENT

Figure 3:
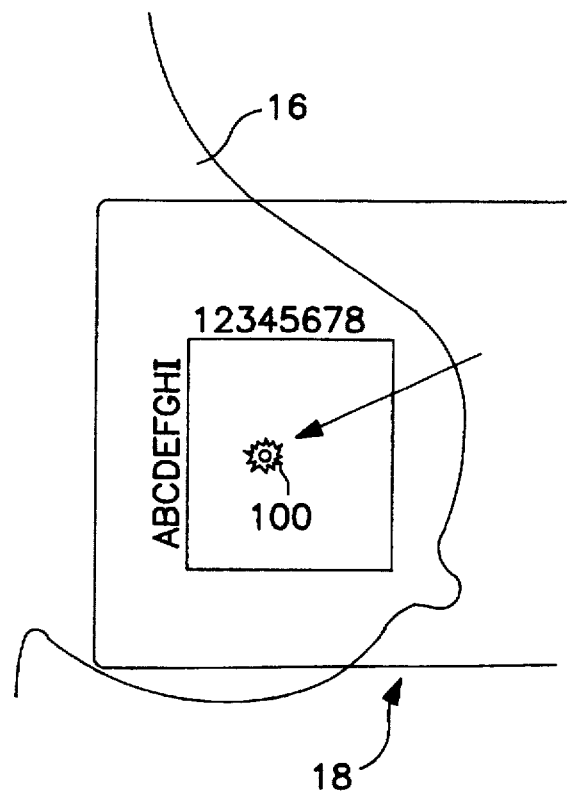
FIG. 3 is a side view of the breast as seen on a mammogram with the breast compressed by a plastic plate with a rectangular window with localization coordinates. A sharpened rod has been passed through the center of the suspected cancer, and is seen end-on as a small circular density.
Figure 4:
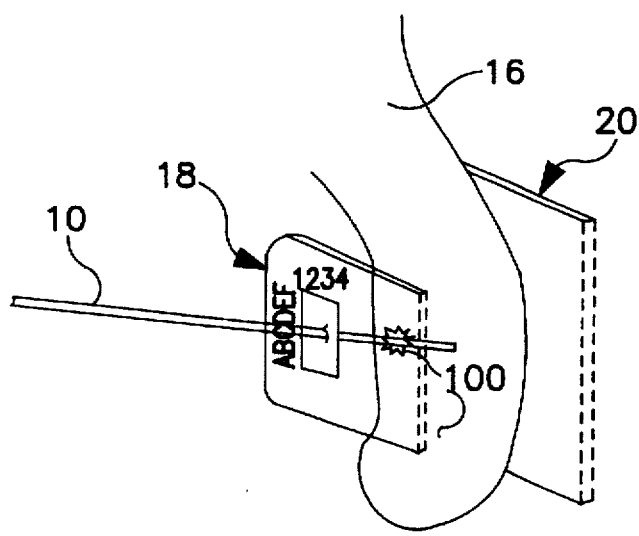
FIG. 4 is a partial front elevation view of the breast compressed in a mammogram machine. A sharpened rod passes though the suspected cancer.
Figure 5:
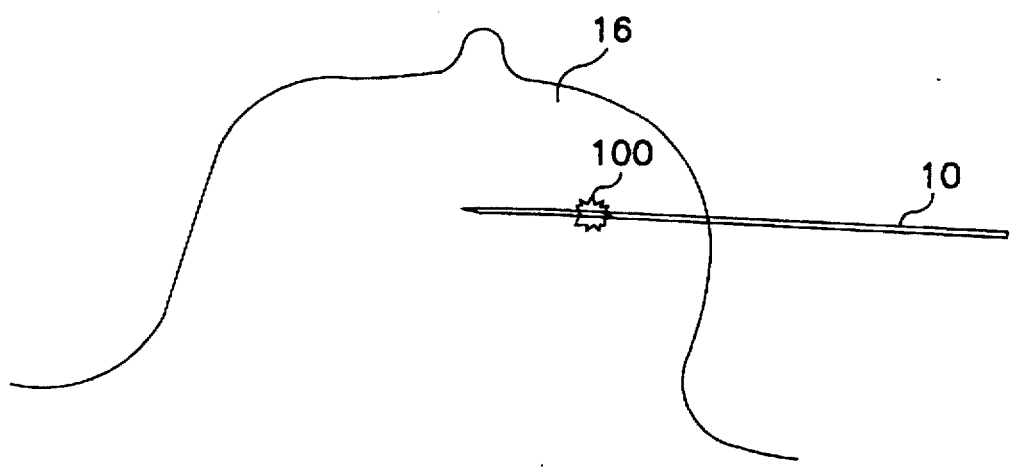
FIG. 5 is a view of the breast as seen on a mammogram taken with the breast compressed from above and below (cc projection). The sharpened rod is now seen penetrating the suspected cancer in profile.
Figure 6:
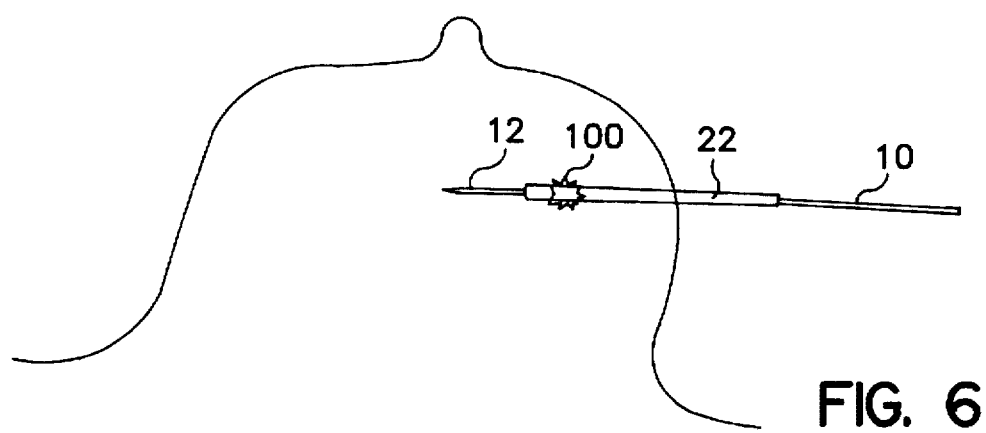
FIG. 6 is a view of the breast as seen on a mammogram (cc projection) with a bevelled tube passed coaxially over the sharpened rod. It is positioned just beyond the suspected cancer.

The instruments employed in the practice of the invention include a sharpened, rigid rod 10 having a conical or bevelled or flattened spear point 12 which can be positioned through a suspected cancer 14 within a breast 16, as shown in FIGS. 3, 4, and 5, with guidance of mammographic x-ray images. A conventional mammographic compression plage 18 and mammographic cassette 20 are depicted in FIG. 4.

Figure 7A:
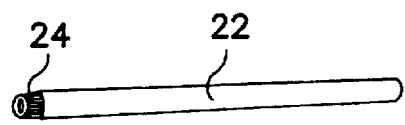
FIG. 7(a) is a partial frontal view of the penetrating end of the bevelled tube. The bevel on the penetrating end enables smooth passage.
Figure 7B:
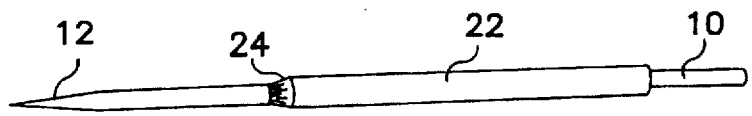
FIG. 7(b) illustrates the sharpened rod extending through the bevelled tube.

A bevelled tube 22, as best shown in FIG. 7, is comprised of a straight hollow cylinder with a sharpened bevelled edge 24 at one end to enable it to slide over the sharpened rod 10 through breast tissue without snagging.

Figure 9:
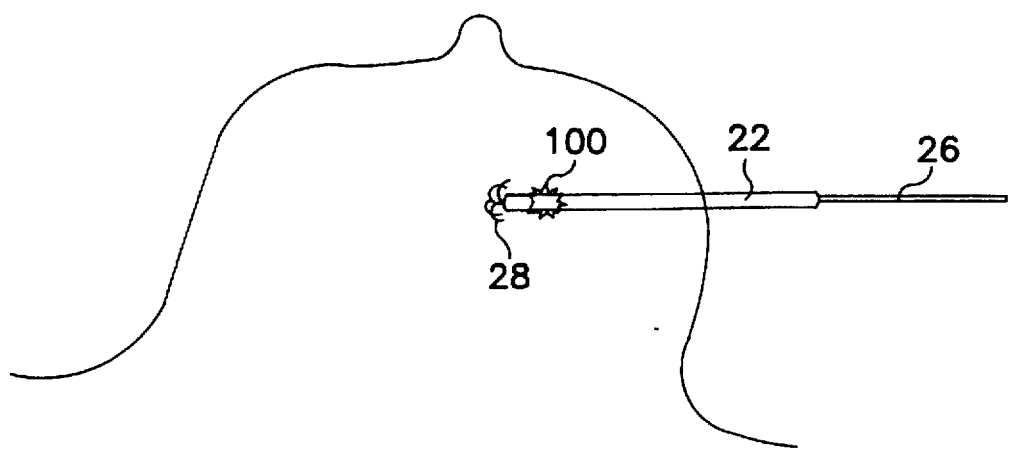
FIG. 9 is a view of the breast as seen on a mammogram (cc projection). A rod with anchor-hooks is passed through the tube. The anchor-hooks are made of flexible, resilient steel wire. As they are extruded out the penetrating end of the bevelled tube, they embed in breast tissue and resume their hooked shape. They form an anchor just distal to the suspected cancer.
Figure 10:
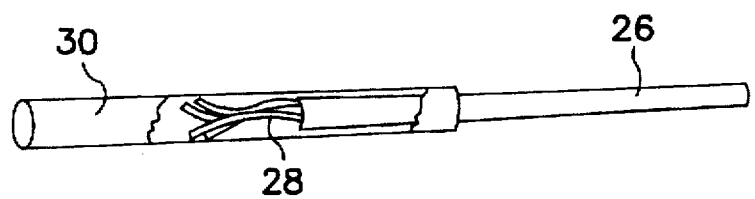
FIG. 10 is a side elevation view, partially broken away, of the rod with anchor-hooks compressed within the lumen of the bevelled tube.

A rigid rod 26 with a plurality of spring steel anchor-hooks 28, as best shown in FIG. 9 which can be compressed within a loading tube 30 shown in FIG. 10 and advanced into the bevelled tube 22, and finally extruded through the penetrating end of the bevelled tube 22 so as to become embedded in adjacent breast tissue. Index or depth markers 29 are provided at the proximal end 31 of the rod 26.

Figure 12:
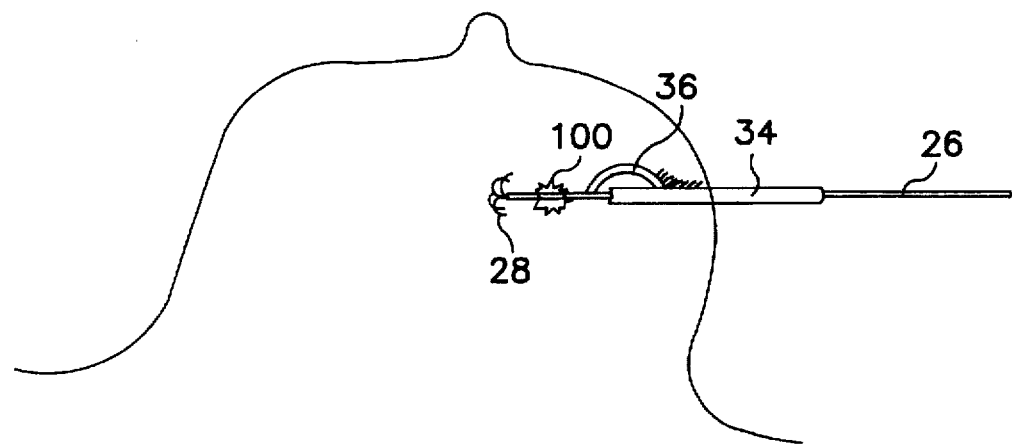
FIG. 12 is a view of the breast as seen on a mammogram (cc projection). A microscalpel (previously disclosed in original patent application of Coaxial Biopsy) passes over the rod and incises a short radial incision to a point proximal to the location of the suspected cancer. This opens a path along the axis of the rod.

A microscalpel 32 as best shown in FIG. 12 has a tubular handle 34 capable of sliding coaxially over the rigid rod 26 to create a short radial incision along the axis of the rigid rod by means of cutting blade 36.

Figure 13:
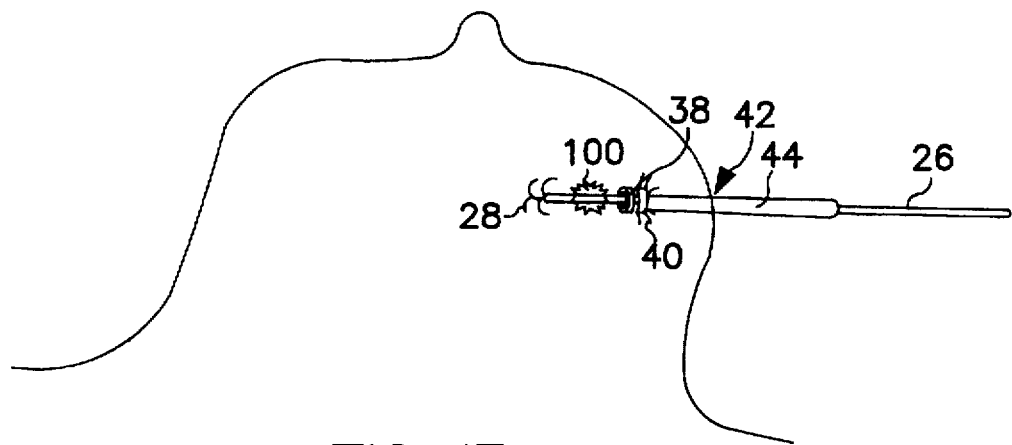
FIG. 13 is a view of the breast as seen on a mammogram (cc projection). A loosely-fitting collar with flexible, resilient spikes, mounted on an inserting tube, passes coaxially over the rod and is positioned just proximal to the suspected cancer.
Figure 14:
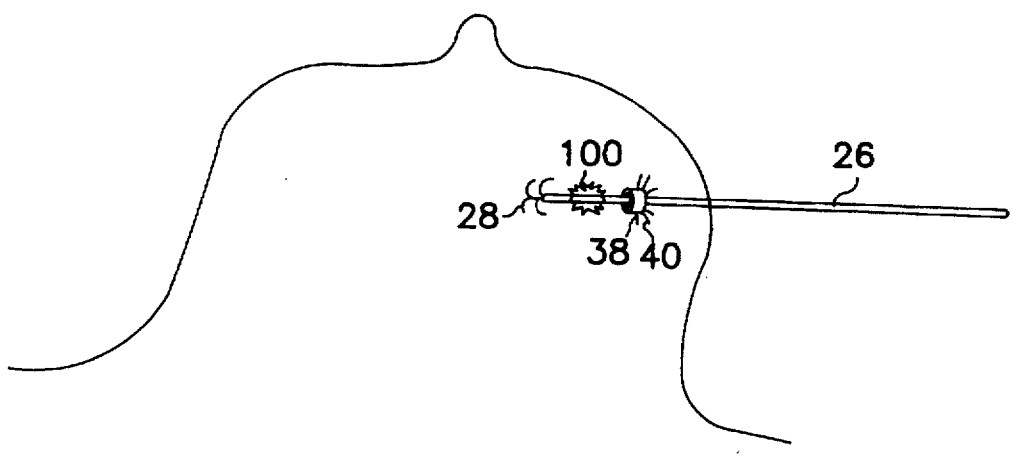
FIG. 14 is a view of the breast as seen on a mammogram (cc projection). The inserting tube has been withdrawn, leaving the spiked collar in position. The flexible spikes, like the anchor-hooks, extend into the adjacent tissue and become embedded.

A spiked collar 38 as best shown in FIGS. 13 and 14 fits loosely over the rigid rod 26. A plurality of spikes 40 are attached to the collar. These spikes are formed of spring steel similar to the anchor-hooks 28 such that they can flex as the collar is inserted into the breast tissue, but straighten out to stabilize the collar within the breast when the collar is positioned along the rod. The rod can move without displacing the collar once the collar is set into position within the breast. The spiked collar is advanced coaxially over the rod by means of an inserting tool 42 having a tube 44 and a collar seat 46. The collar 38 is seated against collar seat 46 during advance over the rod, but it can disengage easily from the inserting tool 42 when the tool is withdrawn and the spikes embed into the breast tissue.

Figure 15:
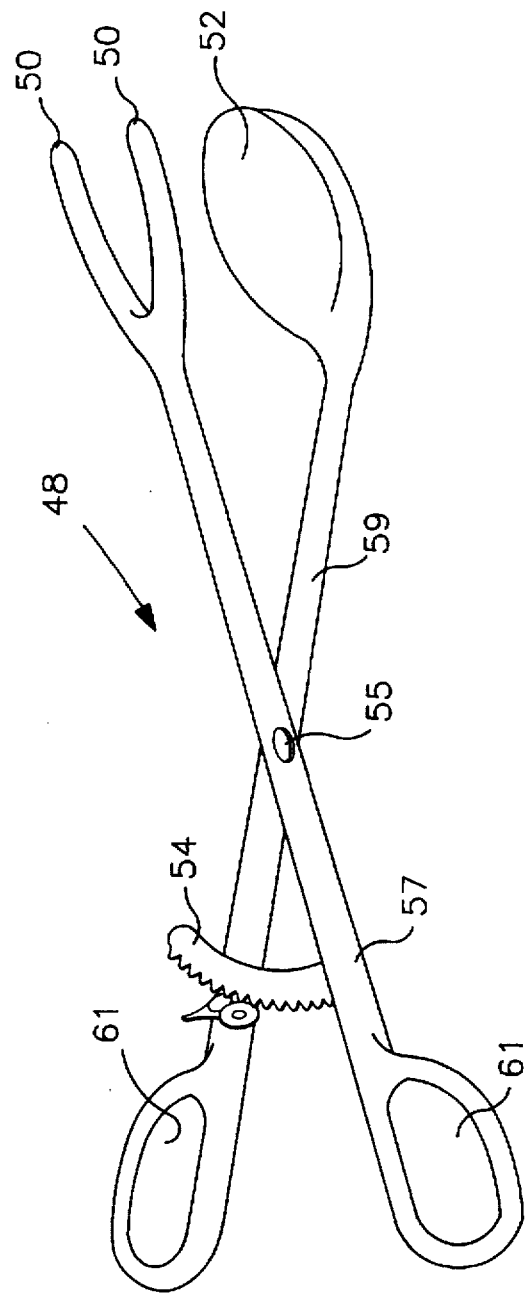
FIG. 15 is a frontal elevation view of stabilizing tongs to compress and stabilize the breast during the biopsy procedure. Holes for a surgeon's thumb and fingers, and a ratchet device to maintain selected compression are shown.
Figure 16:
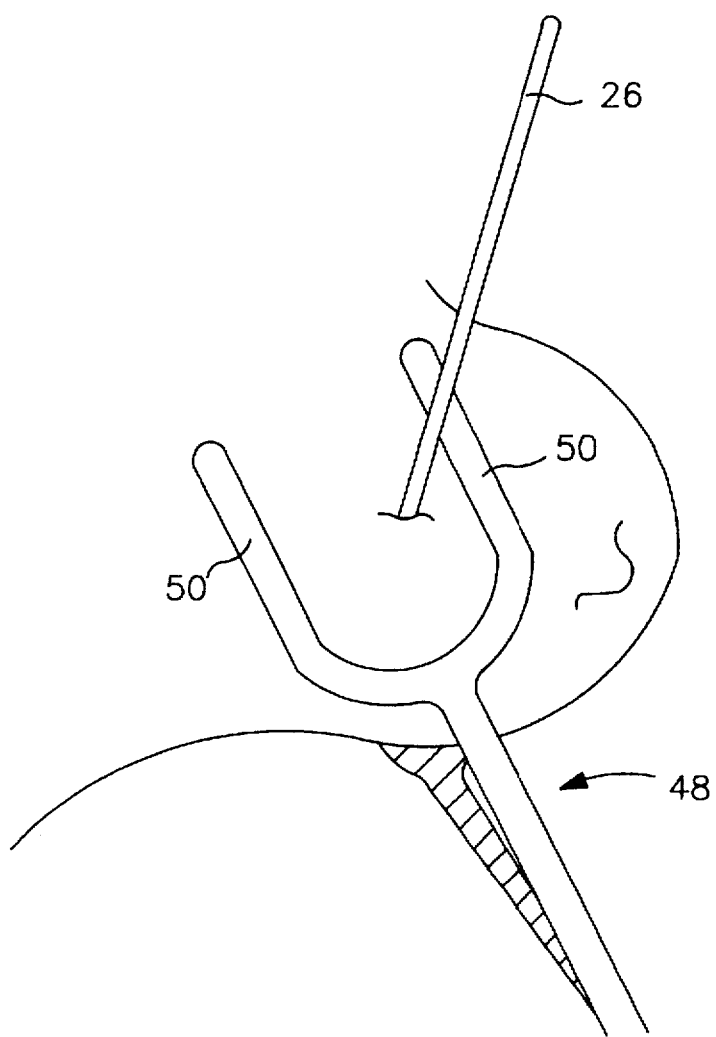
FIG. 16 is a partially frontal view of a breast compressed in a stabilizing tongs in the operating room. Compression is applied along the axis of the rod to foreshorten the distance from skin to lesion.
Figure 17:
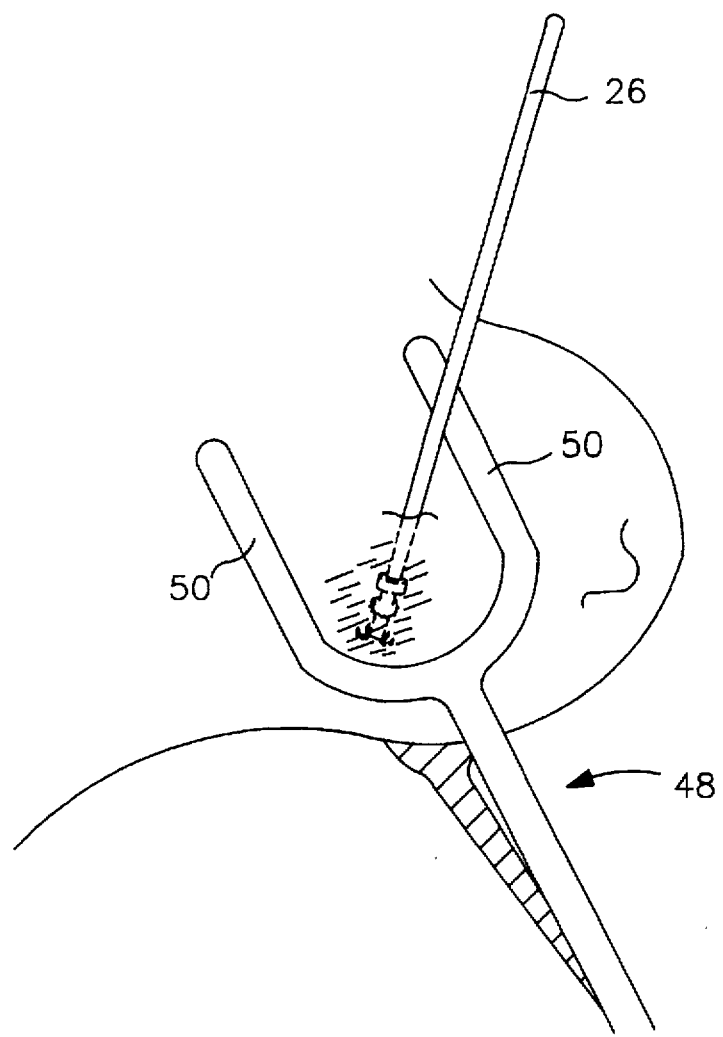
FIG. 17 is a partially frontal view of a breast compressed in a stabilizing tongs in the operating room. The suspected cancer, bracketed by the spiked collar proximally and the anchor-hooks distally, is shown as if the breast tissue were transparent.
Figure 18:
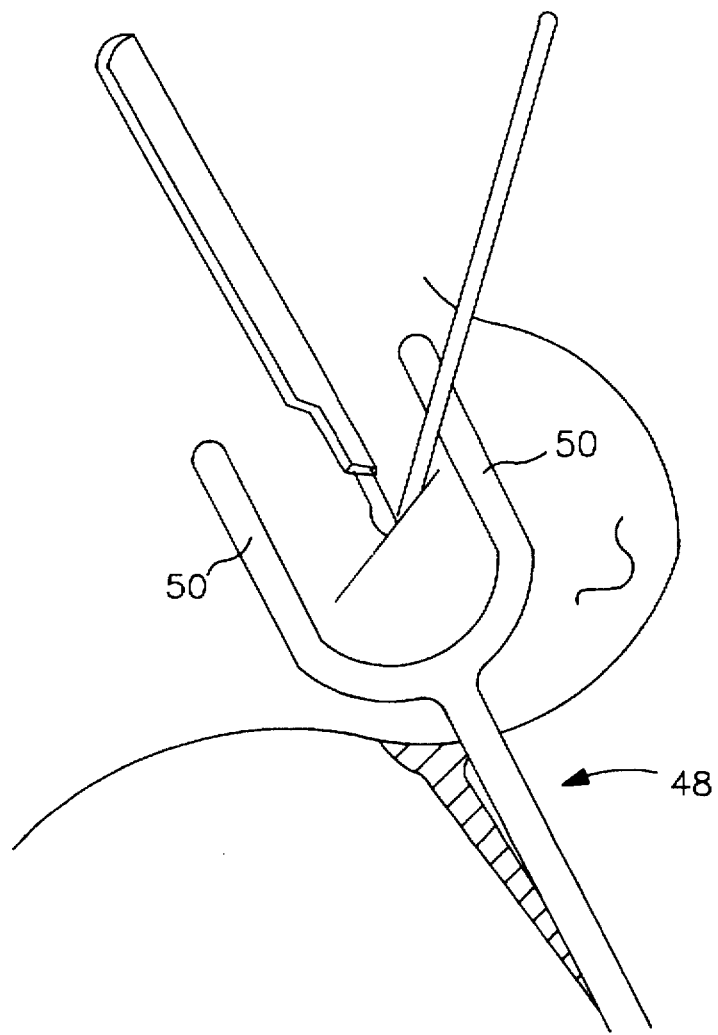
FIG. 18 is a partially frontal view of a breast compressed in a stabilizing tongs. A scalpel makes an incision centered on the rod.

A stabilizing tong instrument 48 best shown in FIG. 15 is capable of stabilizing and compressing the breast so as to facilitate the process of coaxial biopsy. Tongs 50 grasp the breast as would a surgeon's fingers, with compression against a flat spoon-shaped surface 52 maintained by a ratchet mechanism 54. Rivot 55 secures the tongs 57 and 59 for relative rotational movement while finger apertures 61 provide access for the surgeons's fingers.

Figure 26:
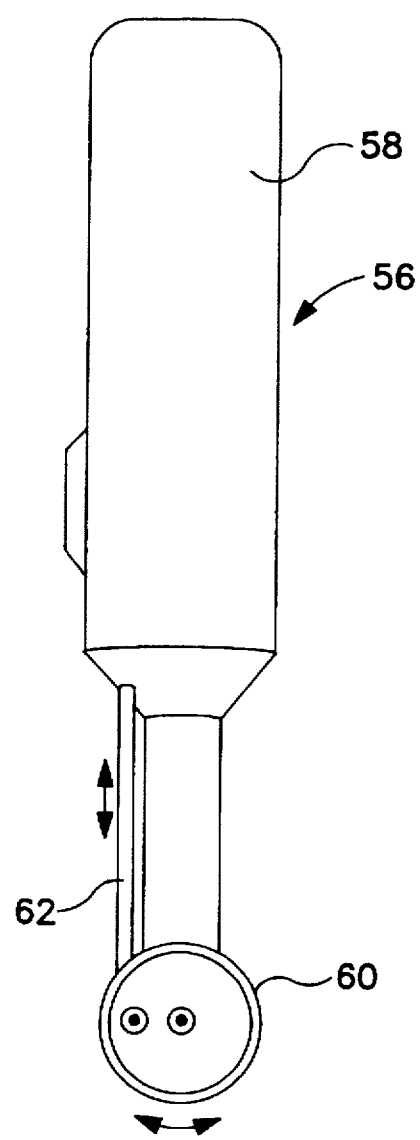
FIG. 26 is a side elevation view of a power scalpel to deepen the skin incision along the axis of the rod.

A power scalpel 56 best shown in FIG. 26. With motor and battery (not shown) in the handle 58, power is delivered to a discoid scalpel blade 60 by a lever 62 with a short, reciprocating movement. The blade moves with a rapid back-and-forth oscillating motion.

A cutting cannula 64 similar to that previously disclosed in the parent application, but with an internal snare mechanism 66 best shown in FIGS. 1, 24 and 27(a) through 27(c). The snare wire 68 rests in an internal circumferential groove 70 near the cutting edge 72 and is maintained therein by a nontoxic adhesive or by the spring action of the wire. The snare wire strands 74 exit through a hole 76 and are maintained in a longitudinal groove 78 along the outer surface of the canula 64 by a nontoxic adhesive or by an outer tube 79 slipped over the external surface of the cutting cannula as shown in FIGS. 27(d)-27(f). An inner rim 81 prevents the tube 79 from moving over the cutting edge of the cannula. Bevel 83 prevents snagging at the distal end. Since the outer tube is maintained in place by the inner rim 81, a hemostat can be used to clamp on the wire strands resting in the groove along the shaft of the cannula. Thus, application of tension to the wire strands will not dislodge them from the groove as the snare loop is closed.

Figure 1:
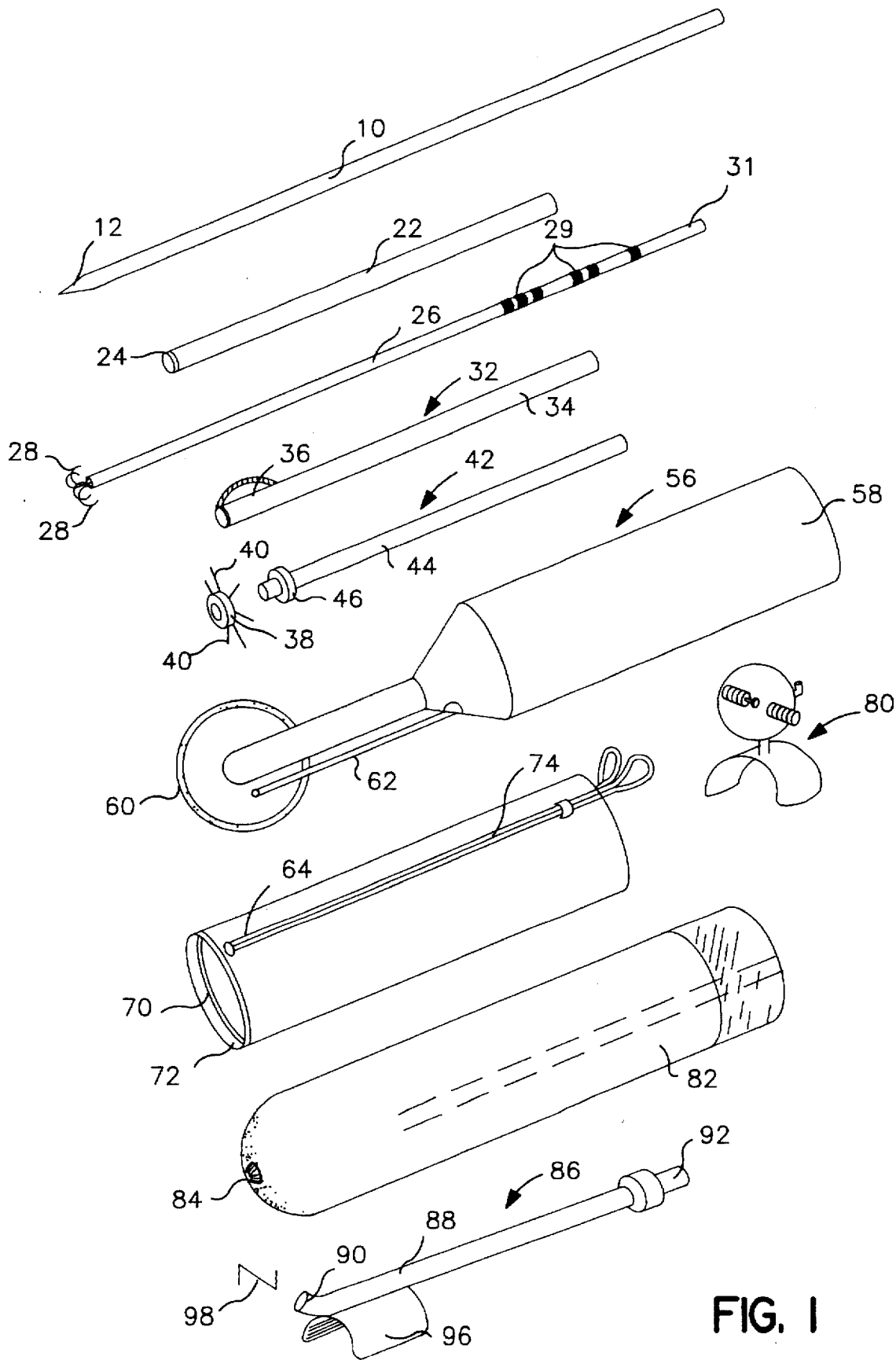
FIG. 1 is an isometric illustration of a plurality of instruments according to the present invention.

The ends of the wire strands are formed into loops which can be connected to a reel mechanism indicated generally by the reference numeral 80 in FIG. 1 to tighten the snare wire, dislodging it from the internal circumferential groove 70. The snare wire can be tightened by the reel mechanism or by a clamped hemostat (not shown) to effect reduction of the size of the snare wire loop and consequently to effect severing of a tissue sample contained within the cannula 64.

A blunt obturator 82 as disclosed in the parent application, has a central longitudinal hole 84 to engage the rigid rod. The obturator fits inside the cannula and maintains it coaxially centered on the axis of the rod. FIG. 27(f) depicts the obturator partially withdrawn to expose the cutting edge of the cannula 72 and create a chamber 85. The central bore 84 for the rigid rod is illustrated together with an eccentric bore 83 that provides for equalization of pressure within the chamber 85.

Figure 28:
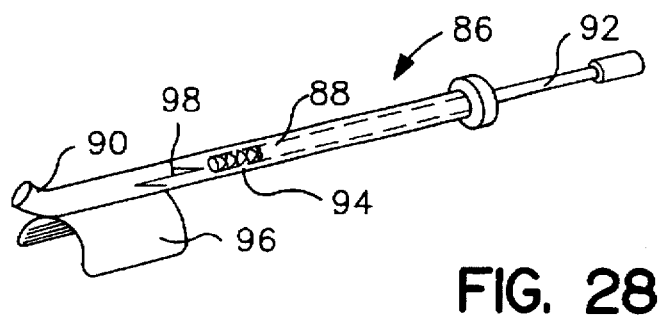
FIG. 28 is a side elevation view partially in cross section showing a clip inserter with a spring steel clip compressed inside the lumen. A stylet with a flexible end-segment is used as a ramrod to move the clip through the lumen and eject it out the penetrating end.
Figure 29:
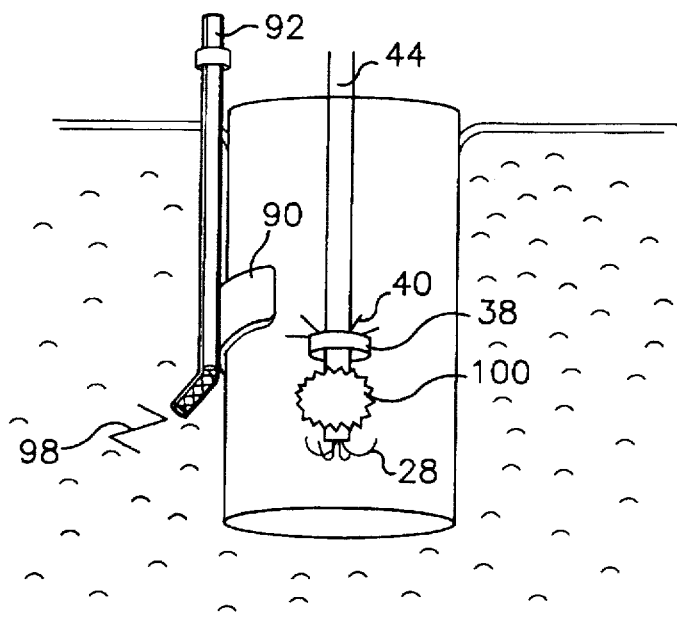
FIG. 29 is a side elevation view in partial cross section showing the spring clip ejected from the clip inserter in breast tissue adjacent to the suspected cancer.
Figure 30A:
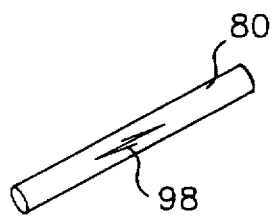
FIGS. 30(a)-(d) shows two configurations of spring clips, compressed within a tube and also uncompressed.
Figure 30B:
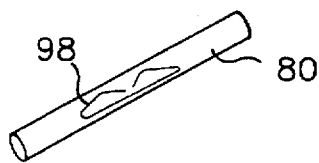
Figure 30C:
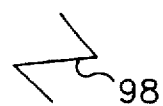
Figure 30D:

A spring clip inserter 86 as best shown in FIGS. 28 and 29 comprises a tube 88 having a short bend 90 at the penetrating end, a plunger 92 with a flexible end 94, and a curved plate 96 to facilitate passage of the clip inserter into the breast along the outer surface of the cutting cannula 64. The spring clips 98 are of spring steel formed into a shape which will lodge in breast tissue without likelihood of spontaneous displacement. When compressed, the clips can be passed through the tubular portion of the clip inserter. FIGS. 30(a) and 30(b) illustrate various configurations of the spring clips 98 in compressed form within a segment of the tube 88. FIGS. 30(c) and 30(d) depict the spring clips in uncompressed form.

The method of Coaxial Biopsy previously disclosed in the parent application enables the surgeon to visualize the location of the suspected cancer along the axis of the penetrating rod by means of a metal target deposited in the lesion. This method allows considerable improvement in precision and accuracy over conventional hook-wire guided biopsy because the surgeon can visualize the target within the specimen as it is removed. However, the disadvantage of this method is that it requires fluoroscopy or ultrasound imaging during the biopsy, whereas conventional hook-wire guided biopsy is usually performed without such additional imaging technology. Ideally, a biopsy method should enable confident localization of the suspected cancer without need for any imaging equipment (fluoroscopic, ultrasound, or stereotactic) during the biopsy.

Figure 2:
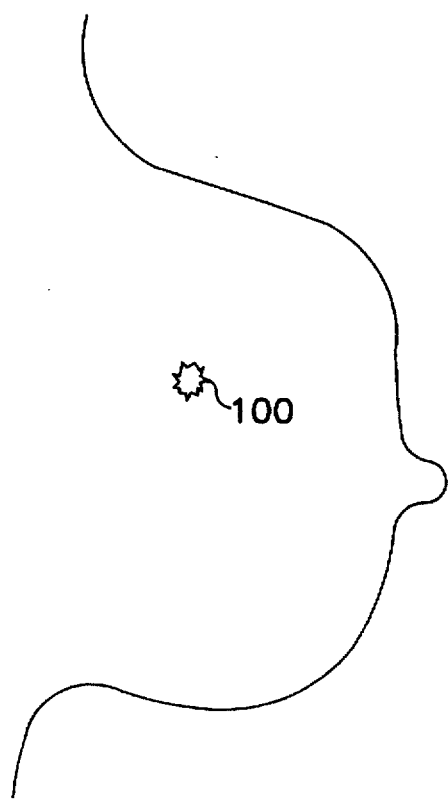
FIG. 2 is a side view of a suspected cancer in a human breast as seen on a mammogram.
Figure 8:
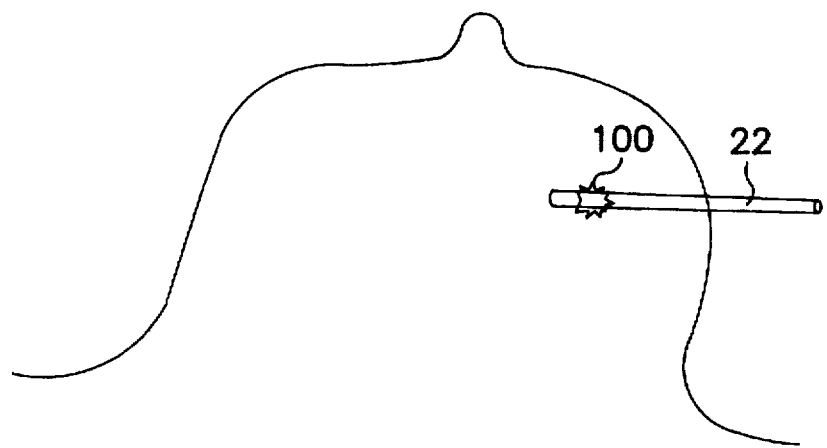
FIG. 8 is a view of the breast as seen on a mammogram (cc projection) with the sharpened rod withdrawn leaving the bevelled tube in position just beyond (distal) to the suspected cancer.
Figure 11:
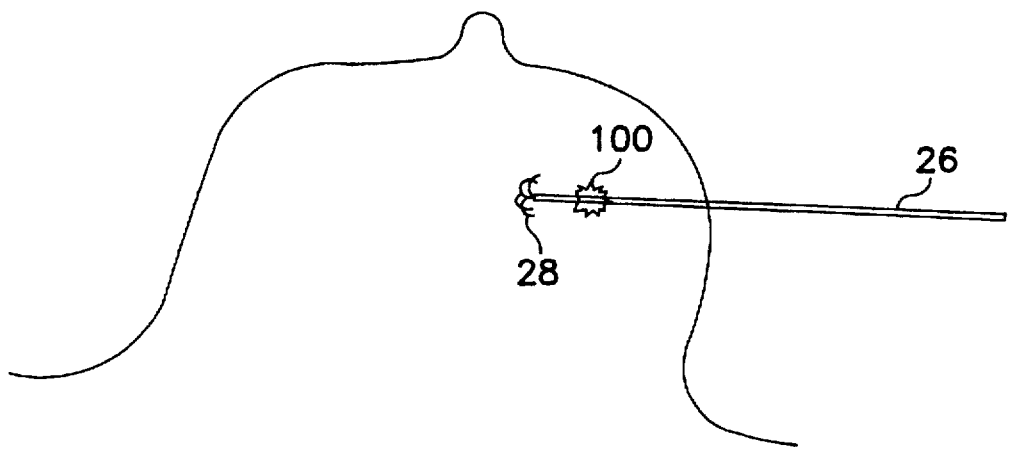
FIG. 11 is a view of the breast as seen on a mammogram (cc projection). The bevelled tube has been withdrawn, leaving the rod with anchor-hooks in position.

The method of the present invention depicted sequentially in FIGS. 2 through 25 provides for the positioning of a sharpened rigid rod (16.5 ga. ideally) through a suspected cancer 100 (FIG. 2) in a manner analogous to the placement of a K-wire (which is a rigid, sharpened rod) through the lesion in the previous disclosure of Coaxial Biopsy. A difference between the present sharpened rod and the commercially available K-wire is that the sharpened points of conventionally available K-wires have a flattened "diamond" shape, like a spear point or a bevel point, but both of these are relatively blunt (without a sharply tapered point). The passage of the rod through breast tissue is facilitated by a long, tapered point which may have a conical, bevelled or spear point shape. The rod, once passed through the center of the suspected cancer, permits a 14 ga. tube to be positioned concentrically over it. With mammographic imaging guidance, the tube is advanced so that the distal end is approximately 1 cm beyond the suspected cancer. When the rod is removed (FIG. 8), the tube functions as a port to deliver another rod 26 with anchor hooks 28 into the breast. When the distal end of the rod with anchor hooks is extruded from the tube, the anchor hooks spring out and embed in the breast tissue, stabilizing the rod such that it can neither advance farther into the breast nor be withdrawn through the suspected cancer. The tube is then removed (FIG. 11). A microscalpel is passed over the rod and incises a short radial incision to the proximal location of the suspected cancer (FIG. 12). This opens a path along the axis of the rod.

With the suspected cancer securely anchored in place near the distal end of the rigid rod with anchor hooks, a loosely-fitting ring or "collar" is positioned concentrically over the rod just proximal to the suspected cancer. The collar is advanced over the rod with the breast still compressed in a mammographic machine. Its progress is monitored with sequential mammographic images as it is positioned approximately 1 cm proximal to the suspected cancer. The collar has flexible short segments or "spikes" of 10 ga. wire radially welded to protrude into the breast tissue and maintain the collar in close relation to the suspected cancer. As the collar is advanced over the rod through the breast tissue, the wire spikes flex. When the collar is deposited in the desired position, the spikes straighten and become embedded in the adjacent breast tissue.

Figure 19:
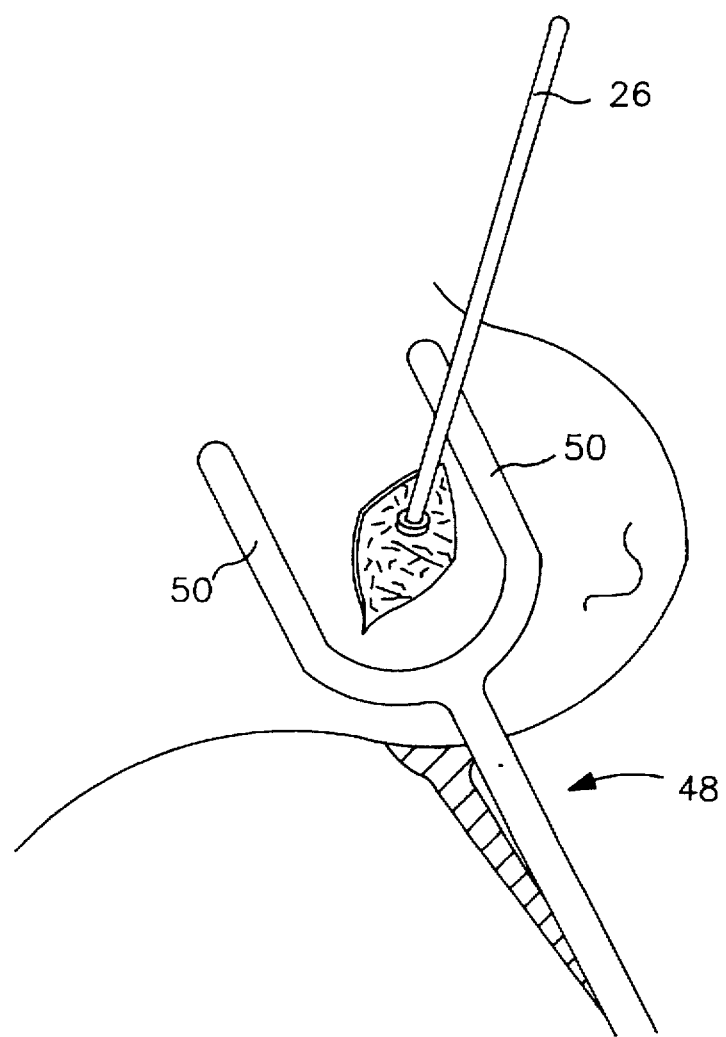
FIG. 19 is a partially frontal view of a breast compressed in a stabilizing tongs. The incision is deepened until the spiked collar is exposed.
Figure 20:
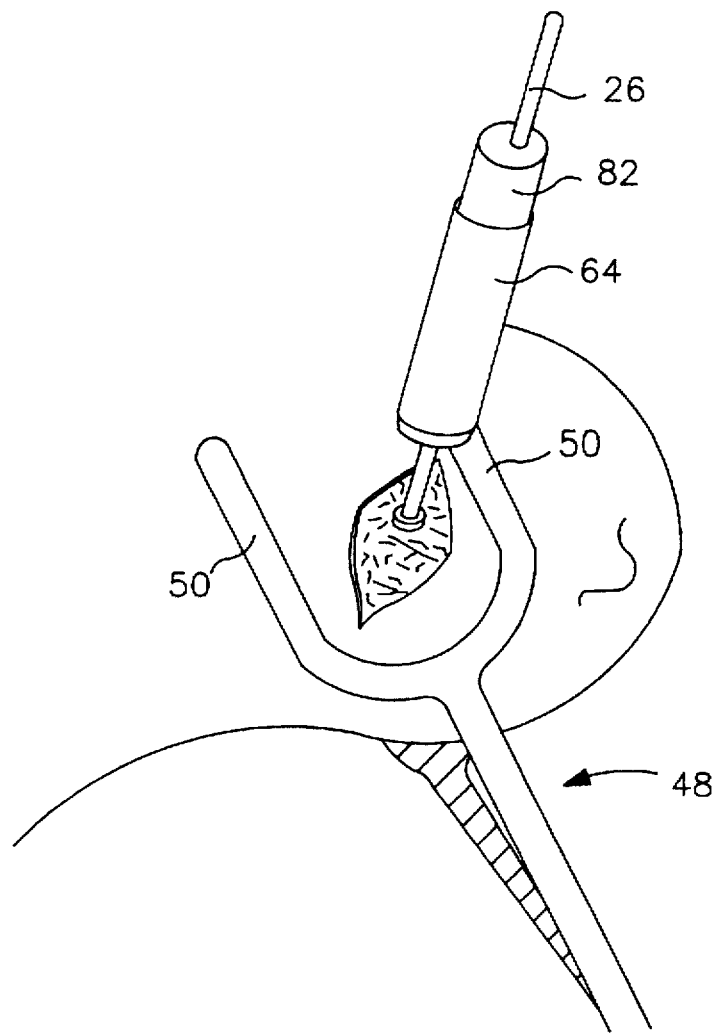
FIG. 20 is a partially frontal view of the cannula/obturator assembly advanced coaxially over the rod.
Figure 21:
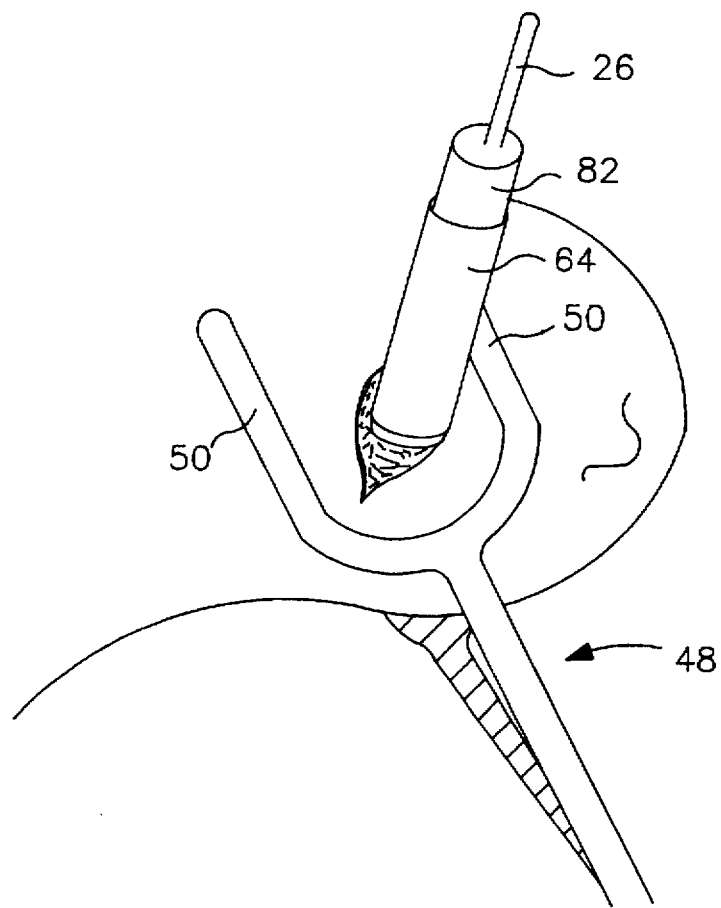
FIG. 21 is a partially frontal view of the cannula/obturator assembly advanced to the depth of the spiked collar. The obturator is then partially withdrawn from the cannula to reveal the cutting edge and the chamber within.
Figure 22:
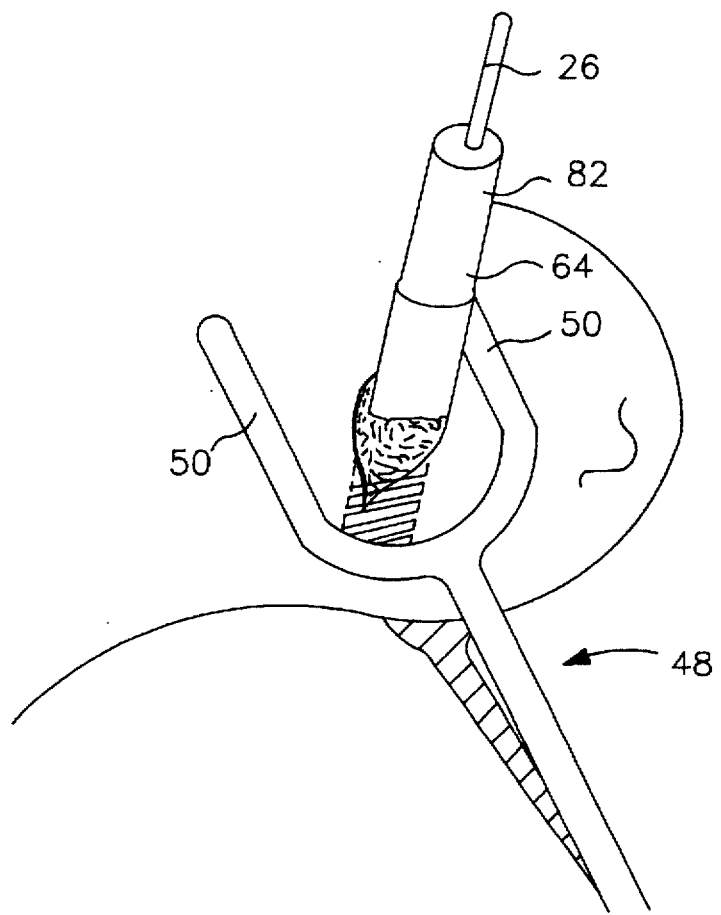
FIG. 22 is a partially frontal view. The cannula has been advanced coaxially along the rod with a back-and-forth rotary cutting movement. A cylinder of tissue around the suspected cancer is cut into the cannula. This is shown as if the cannula and the breast tissue were transparent.
Figure 23:
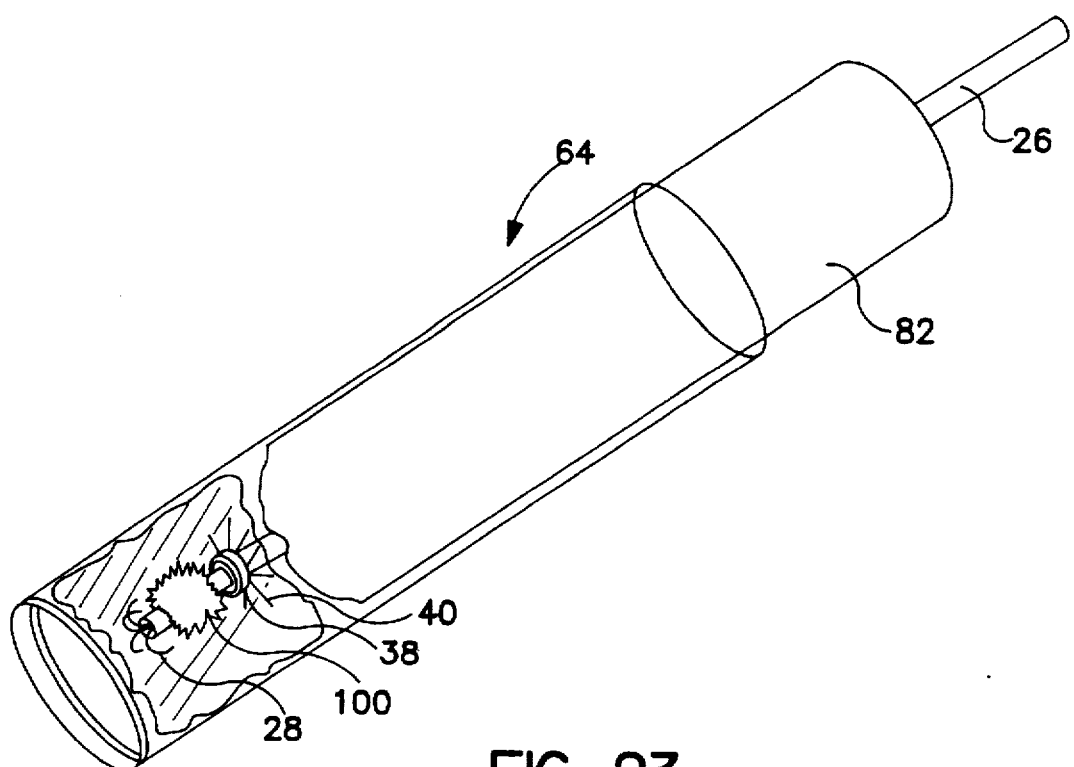
FIG. 23 is a side elevation view, partially in cross section, showing a cylindrical tissue specimen contained within the chamber of the cannula/obturator assembly. The tissue at the base of the cylinder can be amputated by the snare device disclosed in prior patent application or by an internal snare.
Figure 24:
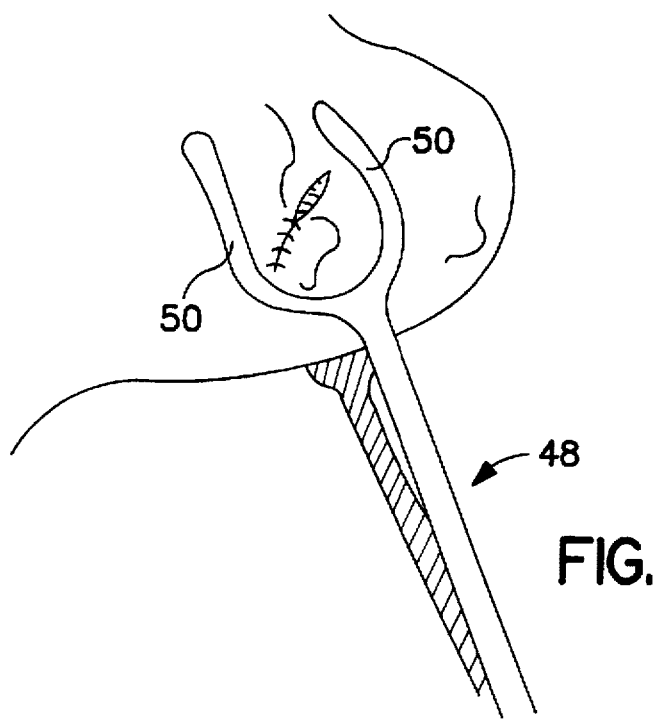
FIG. 24 is a partially frontal view. The cannula/obturator assembly have been removed. The incision is partly closed.

The spiked collar proximally and the anchor hooks distally bracket the suspected cancer between them on the axis of the rod. The rod protrudes from the breast (FIG. 14). As with conventional hook-wire guided biopsy, the rod is covered with a sterile dressing and the patient is transferred to the operating room. There, after sterilizing the skin and injecting anesthetic, the surgeon compresses the breast with the stabilizing tongs (FIG. 15), thus shortening the distance between the skin and the suspected cancer. Then a skin incision is made (FIG. 18), centered on the rod. With the oscillating blade of the power scalpel (FIG. 26) or with conventional scalpel or electrocantery, the incision is deepened into the breast until the spiked collar is exposed under direct visualization (FIG. 19). The cannula/obturator assembly is advanced coaxially over the rod (FIG. 20). The obturator is partially withdrawn and the cannula is advanced with a rotary cutting motion to incise a cylinder of tissue around the rod, until the cutting edge is just beyond the anchor-hooks at the end of the rod (FIG. 21). The surgeon can monitor the progress of the cannula by noting the relation of the proximal end of the obturator to etched markings on the shaft of the rod. Thus, without fluoroscopic, ultrasound, or stereotactic monitoring, the surgeon can reliably begin the circular incision with the cutting cannula about 1 cm proximal to the suspected cancer, and end the circular incision about 1 cm distal to it.

Figure 27A:
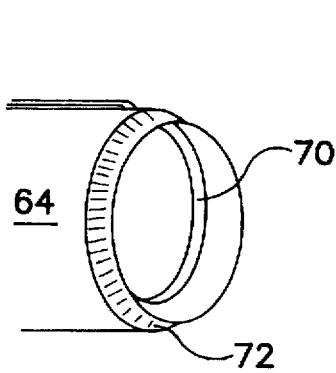
FIGS. 27(a) and (b) are side elevation views of the penetrating end of the cannula, showing the snare wire nested in a circumferential internal groove near the cutting edge. The wire is maintained in place by the spring action of the loop or by a biologically safe adhesive. The wire strands pass through a hole to the exterior of the cannula.
Figure 27B:
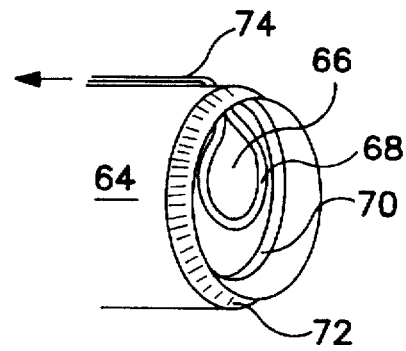
FIG. 27(c) is a plan view of the penetrating end of the cannula. The wire strands are nested in a groove along the shaft where they are also maintained in position by an adhesive or by an external tube slipped over the cannula.
FIG. 27(d) is a side cross-sectional view of the cannula showing the internal circumferential groove, the hole for the wire strands to pass through, and the groove along the shaft of the cannula. A tube is postioned over the cannula to cover the wire strands in the groove along the shaft.
FIG. 27(e) is a plan view of the cannula with obturator partially withdrawn and with the outer tube slipped over the cannula to cover the longitudinal groove along the shaft to maintain the wire strands in the groove.
FIG. 27(f) is a side view in cross section showing the outer tube slipped over the cannula and covering the longitudinal groove.
Figure 27C:
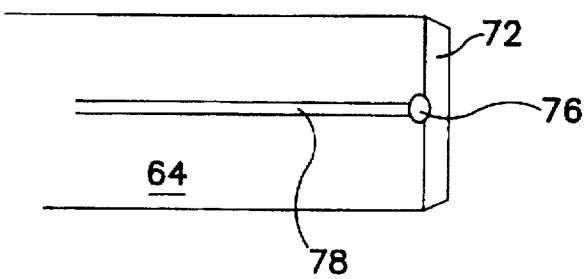
Figure 27E:
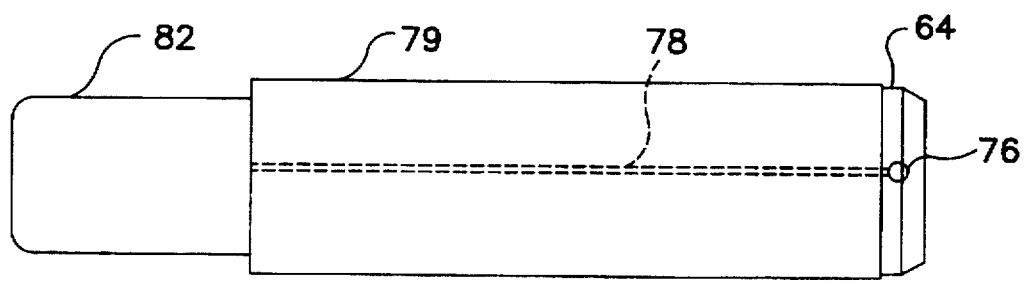
Figure 27F:
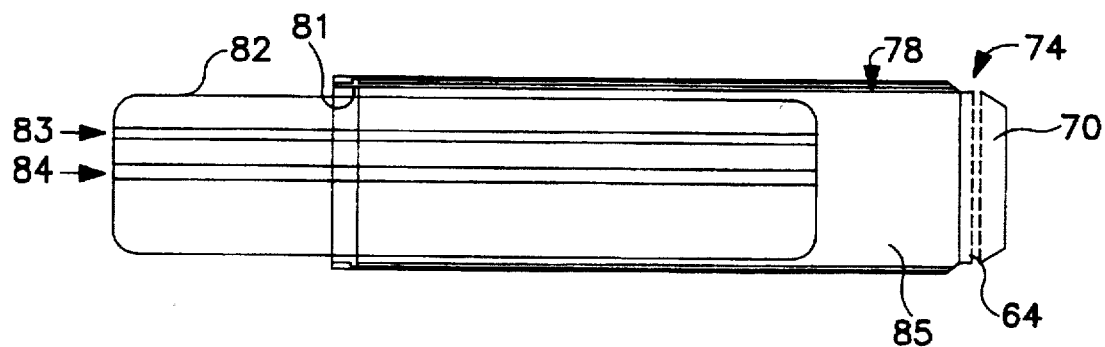
Figure 27D:
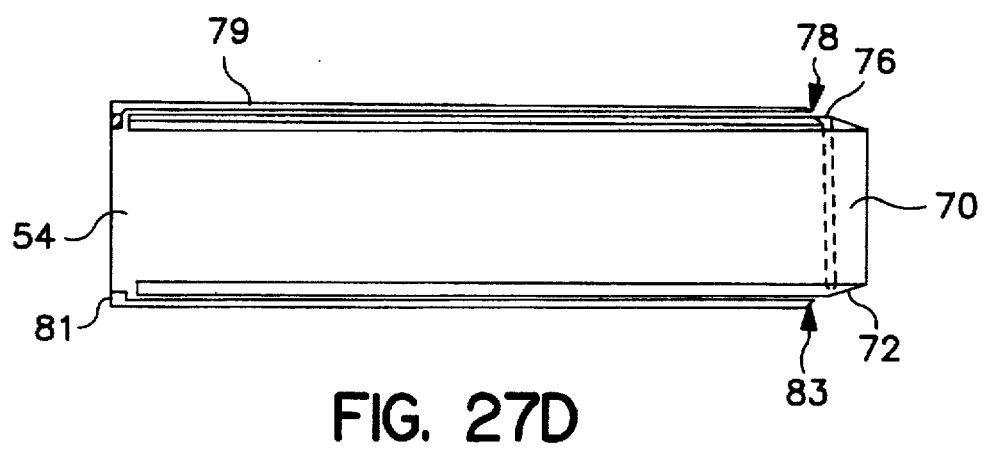

The coaxial cannula is equipped with an internal shallow groove near the cutting edge to retain a snare wire loop (FIGS. 27(a)–27(b)). The cannula is advanced far enough along the rod to ensure that the internally-mounted snare wire is located deep to the anchor-hooks at the end of the rod. The snare wire is made of spring steel and is bent into a loop shape which is slightly compressed as it is positioned inside the cannula. The spring action of the wire maintains it securely in the internal groove. The wire can also be stabilized in the groove by a biologically non-toxic adhesive and the wire can be dislodged from the internal groove by applying tension to the ends of the wire, which pass through a small hole in the cannula. Tension is applied by means of a reel mechanism or by a clamped hemostat. As the snare wire is tightened, the base of the cylinder of tissue is amputated. This completes the incisions separating the specimen from the breast.

A metallic clip is then injected into the breast tissue adjacent to the cannula at the same depth as the suspected cancer, to mark the location of the biopsy (FIGS. 28–30). This clip is designed to spring into a self-retaining shape once it has been extruded from the tubing of the inserting tool, so that it will not dislodge from its position. It is inserted into the breast in a standardized location, e.g., oriented to the nipple. This will enable the radiologist to locate and scrutinize the biopsy site on follow-up mammographic evaluations, and will also indicate the original tumor site in case further therapy is required.

Figure 25A:
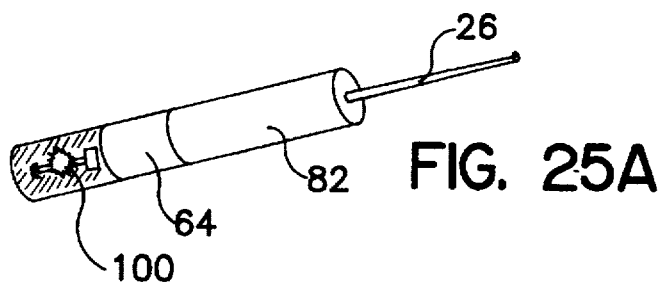
FIGS. 25(a)-(c) is a side elevation view partially in cross section, showing the cannula/obturator assembly removed from the patient (FIG. 25(a)), and recovery of the tissue specimen with the suspected cancer centered within it (FIGS. 25(b)-(c))
Figure 25B:
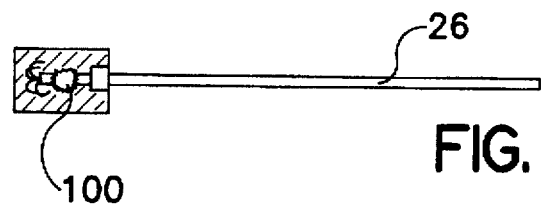
Figure 25C:
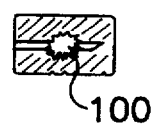

The cannula containing the specimen is then withdrawn from the breast (FIGS. 25(a)–25(c)). The specimen is extruded and then examined with a mammographic x-ray to confirm that the suspected cancer is present within it. The surgeon stops bleeding in the incision either by compression of the breast for several minutes, or by using electrocautery or suture ligatures. The skin incision is then closed, as it is with standard hook-wire guided biopsy.

Having described in detail a preferred embodiment of the invention, it will now be apparent to those skilled in the art that numerous modifications can be made therein without departing from the scope of the invention as defined in the following claims.

What I claim is:

1. A biopsy kit comprising:
   a) a stiff, point-sharpened rod;
   b) a bevel-ended tube adapted to pass coaxially over the stiff, point-sharpened rod;
   c) a stiff anchor rod having a plurality of flexible, resilient anchor hooks located at a distal end thereof, said stiff anchor rod and plurality of flexible anchor hooks being adapted to pass through the bevel-ended tube until the anchor hooks extend beyond the bevel-ended tube;
   d) an insertion tube having a collar seat at an insertion and thereof, said insertion tube being adapted to pass coaxially over the stiff anchor rod; and,
   e) a spiked collar having a plurality of flexible, resilient radially extending spikes adapted to be positioned removably against the collar seat of said insertion tube whereby the stiff, point-sharpened rod can penetrate and impale a suspected cancer with the bevel-ended tube thereafter positioned coaxially over the stiff, point-sharpened rod which can then be withdrawn leaving the bevel-ended tube located with respect to the suspected cancer to provide a guide for the stiff anchor rod that passes through the bevel-ended tube with the anchor hooks extending beyond the bevel-ended tube which can then be withdrawn so that the insertion tube can pass coaxially over the anchor rod with the spiked collar positioned removably against the collar seat of the insertion tube.

2. The biopsy kit of claim 1 further comprising:
   a microscalpel having a longitudinally extending tube adapted to pass coaxially over said stiff anchor rod and an arcuate cutting blade mounted on said longitudingly extending tube at a distal end thereof.

3. The biopsy kit of claim 1 further comprising:
   a powered microscalpel comprising:
   a) a housing having a longitudinal axis;
   b) an electrically powered motor mounted within said housing, said motor providing reciprocatory motion in a direction parallel to the longitudinal axis of the housing;
   c) a circular scalpel having a cutting portion along at least a segment of the circumference of the circular scalpel;
   d) means for rotationally mounting said circular scalpel with respect to said housing; and,
   e) means for imparting the reciprocatory motion of said motor to said circular scalpel to rotate the circular scalpel clockwise and counter-clockwise.

4. The biopsy kit of claim 1 further comprising:
   a breast compression and stabilization instrument having:
   a) a first tong having an intermediate section, a finger receiving aperture at one end of the intermediate section and a pair of tines at the other end thereof;
   b) a second tong having and intermediate section, a finger receiving aperture at one end of the intermediate section and a relatively flat spoon portion at the other end thereof;
   c) means for rotationally securing said first and second tongs together in a scissor-like manner; and,
   d) means for releasably holding said first and second tongs at a fixed position relative to each other so that a desired open distance can be releasably maintained between said tines and said relatively flat spoon portion during breast biopsy.

5. The biopsy kit of claim 1 further comprising:
   a cannula having a cutting end and being adapted to coaxially advance along the stiff anchor rod.

6. The biopsy kit of claim 5 wherein said cannula has a snare loop located within the cannula and wherein the snare loop includes two standing ends that are parallel with respect to said stiff anchor rod and extend along said cannula away from its cutting end whereby when said standing ends are pulled in a direction away from the cutting end of the cannula, the snare loop is closed.

7. The biopsy kit of claim 6 wherein said snare loop standing ends are positioned externally to said cannula and further comprising an outer tube adapted to slip over the cannula and hold the standing ends with respect to the cannula.

8. The biopsy kit of claim 6 wherein the cannula has an internal circumferential groove adjacent to the cutting end of said cannula and wherein said snare loop rests in said internal circumferential groove.

9. The biopsy kit of claim 8 wherein said snare loop is a resilient material having sufficient resiliency to maintain the snare loop in said internal circumferential groove prior to pulling said standing ends.

10. The biopsy kit of claim 8 wherein the cannula internal circumferential groove has an aperture and wherein said snare loop standing ends are positioned externally by passing them through said aperture.

11. The biopsy kit of claim 5 wherein said cannula has an external longitudinal groove and wherein said standing ends are positioned therein.

12. The biopsy kit of claim 5 further comprising:
    a) a flexible, resilient metallic target clip;
    b) a longitudinally extending target clip insertion tube having a longitudinal axis and an arcuate base member adapted to fit on the cannula so that the longitudinal axis of the target clip insertion tube is parallel to the stiff anchor rod; and,
    c) a target clip insertion rod adapted to fit within and move along the longitudinal axis of the target clip insertion tube to drive a flexible, resilient metallic target clip positioned therein along said axis for injection into tissue of a patient.

* * * * *